(12) United States Patent
Jessop et al.

(10) Patent No.: US 7,503,905 B2
(45) Date of Patent: Mar. 17, 2009

(54) VENTING SYRINGE PLUNGER

(75) Inventors: Neil Jessop, Sandy, UT (US); Bruce S. McLean, Sandy, UT (US); Richard Tuttle, Layton, UT (US); Dan J. Bills, Sandy, UT (US); Jared Sheetz, Orem, UT (US)

(73) Assignee: Ultradent Products, Inc., South Jordan, UT (US)

( * ) Notice: Subject to any disclaimer, the term of this patent is extended or adjusted under 35 U.S.C. 154(b) by 250 days.

(21) Appl. No.: 11/242,255

(22) Filed: Oct. 3, 2005

(65) Prior Publication Data
US 2007/0078392 A1 Apr. 5, 2007

(51) Int. Cl.
*A61M 1/00* (2006.01)
(52) U.S. Cl. .................................. 604/122
(58) Field of Classification Search .......... 604/218, 604/187, 181, 60, 219, 82–89, 191, 122, 604/208, 221–224, 232; 433/90; 366/267
See application file for complete search history.

(56) References Cited

U.S. PATENT DOCUMENTS

| | | | |
|---|---|---|---|
| 3,291,128 A | 12/1966 | O'Neil | |
| 3,674,181 A * | 7/1972 | Marks et al. ............. | 222/179.5 |
| 3,677,448 A | 7/1972 | Harris, Sr. et al. | |
| 3,724,076 A * | 4/1973 | Schmitz ................... | 433/90 |
| 3,729,032 A | 4/1973 | Tischlinger et al. | |
| 3,827,147 A * | 8/1974 | Condon ................... | 433/90 |
| 3,834,387 A | 9/1974 | Brown | |
| 4,159,570 A | 7/1979 | Baskas et al. | |
| 4,172,457 A | 10/1979 | Choksi et al. | |
| 4,226,236 A * | 10/1980 | Genese ................... | 604/89 |
| 4,275,730 A | 6/1981 | Hussein | |
| 4,373,535 A * | 2/1983 | Martell ................... | 600/578 |
| 4,492,576 A * | 1/1985 | Dragan ................... | 433/90 |
| 4,619,613 A | 10/1986 | Dragan | |
| 4,632,672 A * | 12/1986 | Kvitrud .................. | 604/222 |
| 4,660,569 A * | 4/1987 | Etherington ............ | 600/578 |
| 4,690,154 A * | 9/1987 | Woodford et al. ....... | 600/578 |
| 4,743,229 A | 5/1988 | Chu | |
| 4,996,468 A | 2/1991 | Field et al. | |
| 5,083,921 A * | 1/1992 | Dragan ................... | 433/90 |
| 5,238,003 A * | 8/1993 | Baidwan et al. ......... | 600/578 |
| 5,328,462 A | 7/1994 | Fischer | |

(Continued)

FOREIGN PATENT DOCUMENTS

CA 1170940 7/1984

(Continued)

*Primary Examiner*—Kevin C Sirmons
*Assistant Examiner*—Michael J Anderson
(74) *Attorney, Agent, or Firm*—Workman Nydegger

(57) ABSTRACT

A venting syringe plunger assembly for use with a syringe system allows for venting of gas from the syringe system during use. The plunger assembly includes a hollow outer sleeve having an interior surface, and an inner stem having an exterior surface. At least a portion of the inner stem is disposed within the outer sleeve so as to be movable (e.g., slidable) within the outer sleeve. A venting passageway is defined between the interior surface of the outer sleeve and the exterior surface of the inner stem. The plunger assembly also includes means for selectively moving the inner stem within the outer sleeve so as to selectively open and close the venting passageway.

19 Claims, 5 Drawing Sheets

U.S. PATENT DOCUMENTS

| | | | |
|---|---|---|---|
| 5,531,703 A * | 7/1996 | Skwarek et al. | 604/187 |
| 5,551,778 A | 9/1996 | Hauke et al. | |
| 5,599,314 A | 2/1997 | Neill | |
| 5,630,800 A | 5/1997 | Blank et al. | |
| 5,643,206 A | 7/1997 | Fischer | |
| 5,665,066 A | 9/1997 | Fischer | |
| 5,697,903 A | 12/1997 | Fischer | |
| 5,770,158 A * | 6/1998 | Eischen et al. | 422/100 |
| 5,873,861 A * | 2/1999 | Hitchins et al. | 604/218 |
| 5,899,881 A * | 5/1999 | Grimard et al. | 604/89 |
| 5,908,054 A | 6/1999 | Safabash et al. | |
| 5,954,688 A * | 9/1999 | Adams et al. | 604/59 |
| 5,957,166 A | 9/1999 | Safabash | |
| 5,971,953 A * | 10/1999 | Bachynsky | 604/90 |
| 6,090,077 A * | 7/2000 | Shaw | 604/195 |
| 6,139,530 A * | 10/2000 | Hiejima et al. | 604/140 |
| 6,234,190 B1 | 5/2001 | Fischer et al. | |
| 6,245,056 B1 * | 6/2001 | Walker et al. | 604/539 |
| 6,273,870 B1 * | 8/2001 | Garvin | 604/110 |
| 6,309,372 B1 | 10/2001 | Fischer et al. | |
| 6,503,084 B2 * | 1/2003 | Evers et al. | 433/226 |
| 6,508,792 B2 * | 1/2003 | Szames et al. | 604/237 |
| 6,530,906 B2 * | 3/2003 | Hu | 604/218 |
| 6,592,251 B2 | 7/2003 | Edwards et al. | |
| 6,641,394 B2 * | 11/2003 | Garman | 433/881 |
| 6,685,063 B2 | 2/2004 | Brugner | |
| 6,921,380 B1 | 7/2005 | Epstein et al. | |
| 7,168,847 B2 | 1/2007 | Frei et al. | |
| 2001/0016703 A1 | 8/2001 | Wironen et al. | |
| 2001/0037091 A1 * | 11/2001 | Wironen et al. | 604/236 |
| 2002/0198499 A1 * | 12/2002 | Hu | 604/218 |
| 2004/0122359 A1 | 6/2004 | Wenz et al. | |
| 2005/0105385 A1 | 5/2005 | McGill et al. | |
| 2005/0182371 A1 * | 8/2005 | Wagner et al. | 604/218 |
| 2006/0116644 A1 * | 6/2006 | Norton | 604/187 |
| 2006/0142701 A1 * | 6/2006 | Thorne et al. | 604/218 |
| 2006/0253081 A1 * | 11/2006 | Paulos et al. | 604/187 |
| 2007/0078392 A1 * | 4/2007 | Jessop et al. | 604/122 |
| 2007/0112308 A1 * | 5/2007 | Kay et al. | 604/187 |

FOREIGN PATENT DOCUMENTS

| | | |
|---|---|---|
| GB | 714983 | 9/1954 |
| GB | 879427 | 10/1961 |
| JP | 5192360 | 8/1993 |
| JP | 2004188047 | 7/2004 |
| JP | 05186026 | 7/2005 |
| WO | WO 9507721 | 3/1995 |
| WO | WO 9848869 | 11/1998 |
| WO | WO 9965597 | 12/1999 |
| WO | WO 02076374 | 10/2002 |

* cited by examiner

VENTING SYRINGE PLUNGER

BACKGROUND OF THE INVENTION

1. The Field of the Invention

The present application is directed to devices for mixing and dispensing medical and dental compositions. More particularly, the application is directed to methods and devices for mixing and dispensing multi-part medical and dental compositions while permitting air or gas to be vented.

2. The Relevant Technology

Many modern formulations are packaged in two parts, often known as A and B components. Upon mixing, the A and B components typically undergo a chemical reaction which causes the resultant composition to "set up" or "cure" in some desired manner. In the dental field, for example, several two-part formulations currently enjoy wide use, such as glass ionomer cements and resinous luting cements. Dental impression materials are also typically made using A and B components.

In order to function properly, it is important that the A and B components of two-component systems be mixed together rapidly and thoroughly and in the right proportions. Failure to rapidly mix the components can result in loss of valuable working time with the resultant composition, and can impact the ability to obtain a thorough mix as the composition may begin to set up unevenly. Failure to mix thoroughly can result in a composition having less than optimum characteristics. For example, if a poorly mixed composition is used as a cement, it is possible that portions of the cement will fail to reach the chemical strength required for a long-term bond.

Problems of obtaining rapid and uniform mixing are often complicated by differences in the A and B components. It is often necessary to mix two liquids, while other times it is necessary to mix a powder with a liquid. Sometimes there are equal amounts of the A and B components, but in other cases there is more of one component than another. Additionally, the two components may have similar viscosities or widely differing viscosities. Components having greatly differing viscosities or other physical properties are typically harder to mix than components having similar physical properties.

One method employed for mixing multiple components has been simple mechanical mixing, through the use of a mixing bowl or pad and a stir instrument such as a spatula. This method tends to be somewhat messy and time consuming. It also is difficult at times to determine whether the mixing has been sufficiently thorough.

An alternative and generally superior system uses two syringes, and optionally a coupler between the two syringes. The distal end of each syringe is coupled to the coupler or directly to the other syringe. The components may be passed back and forth between the syringes in order to mix the components.

It is difficult in many instances to prevent formation of small air or gas bubbles in the mixed composition. With some components, an air or gas bubble may develop within the syringe during storage. In addition, gaseous products may be generated as a result of mixing some A and B components. Such entrapped air or gas bubbles, either within the separate syringes before mixing or within the mixed composition after mixing, can be detrimental.

It would be an advantage to provide a plunger assembly for use with a syringe system that would allow the user to vent air and/or gas bubbles when needed (e.g., before and/or after mixing).

SUMMARY OF THE INVENTION

The present invention is directed to a venting syringe plunger assembly for use with a syringe system. The plunger assembly includes a hollow outer sleeve having an interior surface, and an inner stem having an exterior surface. At least a portion of the inner stem is disposed within the outer sleeve so as to be movable (e.g., slidable) within the outer sleeve. A venting passageway is defined between the interior surface of the outer sleeve and the exterior surface of the inner stem. The plunger assembly also includes means for selectively moving the inner stem within the outer sleeve so as to selectively open and close the venting passageway.

In one example, means for selectively moving the inner stem within the outer sleeve may comprise a cam member disposed near a proximal end of the inner stem and outer sleeve. The cam member is operable to move the inner stem within the outer sleeve, selectively opening and closing the venting passageway, which allows air or other gas trapped within a syringe barrel to escape and be vented through the venting passageway.

The inner stem may include a head near the proximal end of the inner stem, while the outer sleeve may include a flange near its proximal end. The head of the inner stem may be disposed outside the outer sleeve. The cam member may be slidably disposed between the head of the inner stem and the flange of the outer sleeve. The cam member may further include a ramped lever (e.g., an area of the cam having increased thickness relative to another portion of the cam) such that as the cam member is slid between the head and the flange, the ramped lever of the cam pushes the head apart from the flange, which causes the inner stem to slide relative to the outer sleeve. The sliding of the inner stem within the outer sleeve selectively opens or closes the venting passageway. For example, pulling the inner sleeve into the outer sleeve may close the venting passageway, while pushing the inner sleeve to extend from the outer sleeve may open the venting passageway (or vice versa).

The outer sleeve may include means for sealing the outer sleeve of the plunger assembly against an inner surface of a syringe barrel. In one example, sealing means may comprise a groove formed near a distal end of the outer sleeve and an elastomeric seal (e.g., an O-ring) seated within the groove. In another embodiment, sealing means may comprise a V-cup seal formed at a distal end of the outer sleeve.

The inner stem also includes means for forming a seal with the interior surface of the outer sleeve, so as to allow a user to close the venting passageway. For example, the distal end of the inner stem may include a portion (e.g., a tapered portion or a luer cone) that selectively forms a seal with the distal end of the interior surface of the outer sleeve. Movement of the inner stem within the outer sleeve opens and closes the seal, selectively opening and closing the venting passageway.

In another example, means for selectively moving the inner stem within the outer sleeve may comprise threads formed on the exterior surface (e.g., near a proximal end of the inner stem) and corresponding engagement grooves formed in the interior surface (e.g., also near a proximal end of the outer sleeve) such that rotation of the inner stem within the outer sleeve longitudinally moves the inner stem within the outer sleeve so as to selectively open and close the venting passageway.

In a related method for using the vented plunger assembly, a syringe-to-syringe o m mixing system may be provided. The mixing system may include a first syringe with an associated first plunger loaded with a first component, and a second syringe with an associated second plunger loaded with a second component. At least one of the first or second plungers comprises a vented plunger assembly as described above. The first and second syringes are coupleable together so that the barrel of the first is in fluid communication with the barrel of the second (and vice versa). The first and second plungers are then alternatingly pushed so as to pass the first and second components between the first and second syringes in order to mix the first and second components together. The first and second components may both be liquids, or one may be a liquid while the other is a powder. Once the components have been mixed together as desired, the venting passageway of the at least one venting plunger assembly may be opened so as to vent any air or gas contained within the syringe barrels. The syringes may then be separated, and the mixed composition may be dispensed either directly out of the syringe or through a dispensing tip that may be coupled to the syringe containing the mixed composition. Any trapped air or gas may be vented again or for the first time if needed (e.g., additional air may have been introduced into the syringe barrel when coupling a dispensing tip), or additional gas may be generated as a result of mixing multiple components together over time.

These and other benefits, advantages and features of the present invention will become more full apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

I. Introduction

Figure 1A:
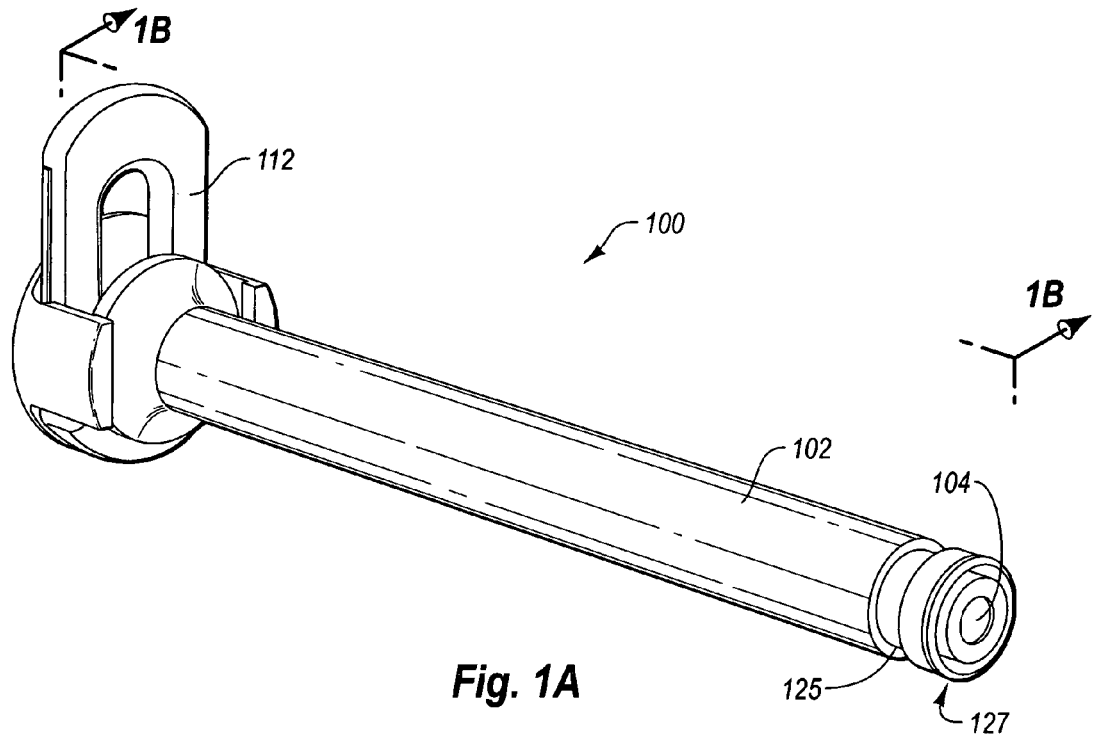
FIG. 1A is a perspective view of an exemplary vented plunger assembly.

A detailed description of the invention will now be provided with specific reference to figures illustrating various exemplary embodiments. It will be appreciated that like structures will be provided with like reference designations.

II. Exemplary Vented Plunger Assemblies

FIGS. 1A-1D illustrate an exemplary vented plunger assembly 100. Vented plunger assembly 100 includes a hollow outer sleeve 102, an inner stem 104, a venting passageway 106, and means for selectively moving the inner stem within the outer sleeve so as to selectively open or close the venting passageway 106. Hollow outer sleeve 102 includes an interior surface 108, while inner stem 104 includes an exterior surface 110. The venting passageway 106 is bounded and defined by the interior surface 108 of the outer sleeve 102 and the exterior surface 110 of the inner stem 104. Venting passageway 106 is shown running substantially parallel to the longitudinal axis A of plunger assembly 100, allowing air or other gas to be vented from a barrel of a syringe associated with the plunger 100 through venting passageway 106 and out the proximal end 101 of plunger assembly 100.

Figure 1B:
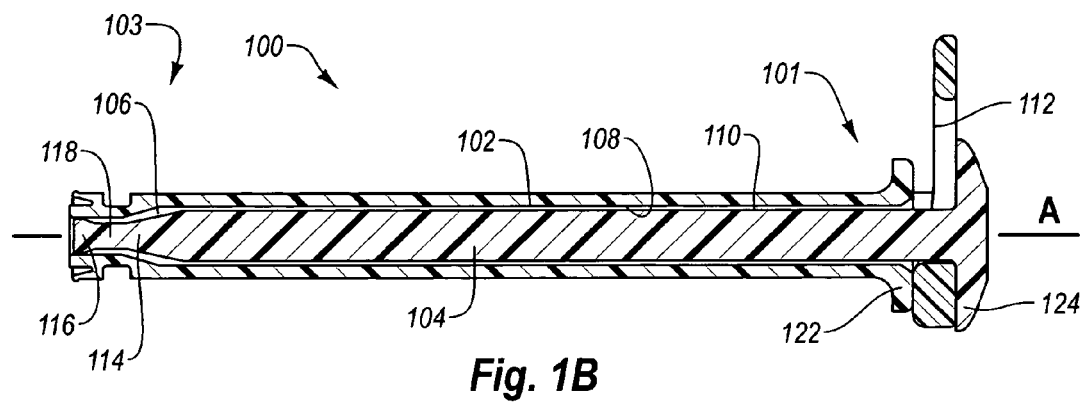
FIG. 1B is a cross-sectional view of the vented plunger assembly of FIG. 1A in a closed position.
Figure 1C:
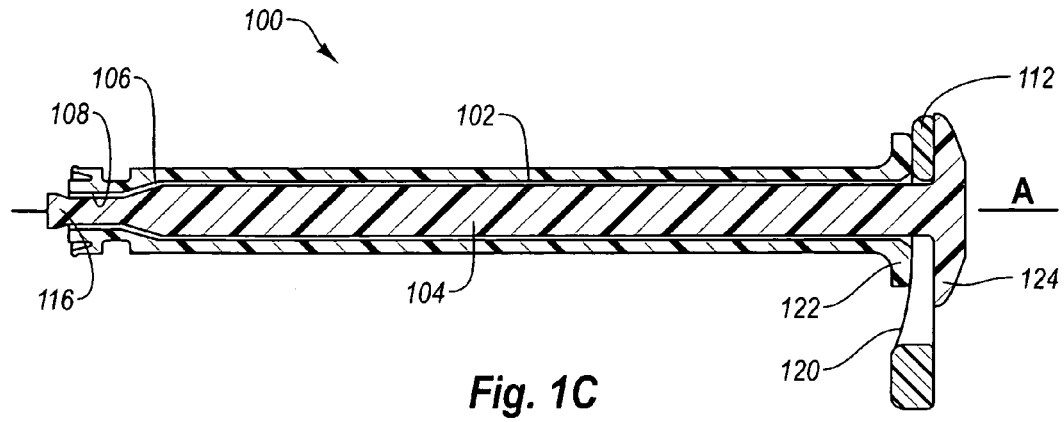
FIG. 1C is a cross-sectional view of the vented plunger assembly of FIG. 1A in an open position.
Figure 1D:
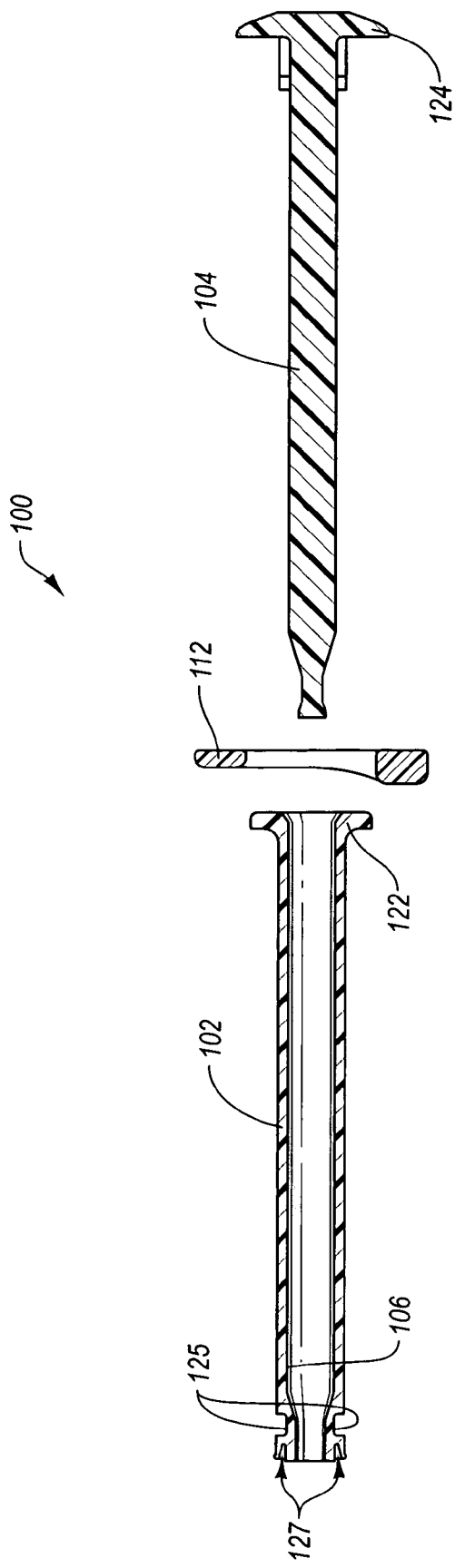
FIG. 1D is an exploded view of the vented plunger assembly of FIG. 1A.

FIG. 1B is a cross-sectional view of the venting plunger assembly 100 with venting passage 106 in a closed and sealed position. Plunger assembly 100 includes a cam member near the proximal end of inner stem 104. In the illustrated embodiment, cam member 112 is retained by inner stem 104 such that stem 104 passes through cam member 112. Cam member 112 as illustrated is slidable in a plane substantially perpendicular to the longitudinal axis A of inner stem 104. Cam member 112 is one example of means for selectively moving inner stem 104 within outer sleeve 102. Movement of stem 104 within sleeve 102 selectively opens and closes the seal between the stem 104 and the sleeve 102 at the opposite distal end 103 of assembly 100. For example, when cam member 112 is in the position as illustrated in FIG. 1B, inner stem 104 is withdrawn into sleeve 102, closing the seal between distal portion 116 of inner stem 104 and interior surface 108 of outer sleeve 102, which closes venting passageway 106. When cam member 112 is in the position as illustrated in FIG. 1C, inner stem 104 is free to be pushed further into sleeve 102, opening the seal and venting passageway 106. Sliding cam member 112 back to the position of FIG. 1B withdraws the inner stem 104 to be substantially flush with the distal end of or within outer sleeve 102 so as to reseal venting passageway 106.

The distal end 103 of inner stem 104 is configured to form a seal with interior surface 108 of sleeve 102. In the illustrated embodiment, the inner stem 104 is conically tapered in two portions. Transition portion 114 is conically tapered so as to have a cross sectional diameter that decreases towards the distal end 103 of stem 104. Distal portion 116, located at the distal end 103 of stem 104, is conically tapered so as to have a cross sectional diameter that increases in the direction of the distal end 103 of stem 104. Transition portion 114 and distal portion 116 are connected by an intermediate portion 118 of substantially constant cross sectional diameter. A seal between the inner stem 104 and the interior surface 108 of outer sleeve 102 is formed when distal portion 116 contacts interior surface 108, as seen in FIG. 1B. In this configuration, the seal is closed, preventing air or another gas from entering venting passageway 106 and being vented.

From FIGS. 1B and 1C, it can be seen that cam member 112 may be slid so that the thickened end of ramped lever 120 is no longer sandwiched between flange 122 of outer sleeve 102 and head 124 of inner stem 104. Because the portion of cam member 112 that is then between flange 122 and head 124 is thinner than the thickened end of ramped lever 120, the inner stem 104 may be pressed further into outer sleeve 102, as seen in FIG. 1C, again sandwiching cam member 112 between flange 122 and head 124. In this new position, distal portion 116 of inner stem 104 is pushed out through the distal end 103 of outer sleeve 102, which opens venting passageway 106, allowing air or other gas to enter distal end 103 of plunger assembly 100 and be vented through venting passageway 106.

From the open configuration illustrated in FIG. 1C, the plunger assembly 100 may be returned to the closed configuration (e.g., after any air or gas has been vented) by simply sliding cam member 112 back to the position illustrated in FIG. 1B. Ramped lever 120 of cam member 112 forces head 124 apart from flange 122, causing portion 116 to pull back into outer sleeve 102, resealing portion 116 against interior surface 108.

Outer sleeve 102 may include means for sealing outer sleeve 102 of plunger assembly 100 against an inner surface of a syringe barrel (not shown). In one example, sealing means may comprise a groove 125 formed near distal end 103 of the outer sleeve 102 and an elastomeric seal (e.g., an O-ring, not shown) seated within groove 125. Another example of sealing means is a V-cup seal 127 formed at a distal end of the outer sleeve. Further details of a suitable V-cup seal are found in U.S. Pat. No. 6,398,763, herein incorporated by reference with respect to its disclosure of V-cup seals. In the illustrated embodiment, outer sleeve 102 includes both a groove for an O-ring and a V-cup seal for increased protection against leaks between the plunger and a syringe barrel. Other embodiments may include only one sealing means.

Figure 2A:
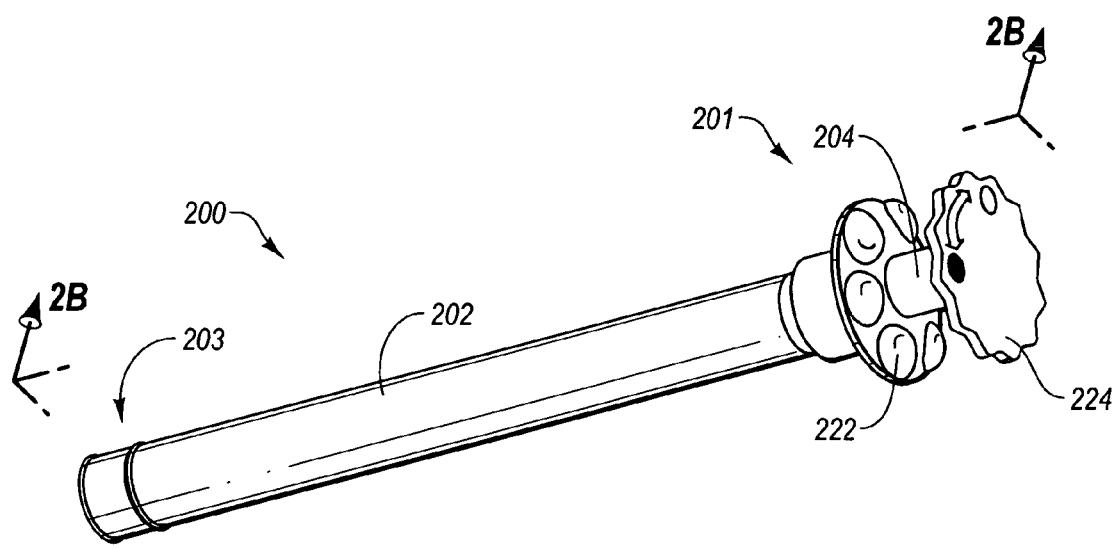
FIG. 2A is a perspective view of another exemplary vented plunger assembly.
Figure 2B:
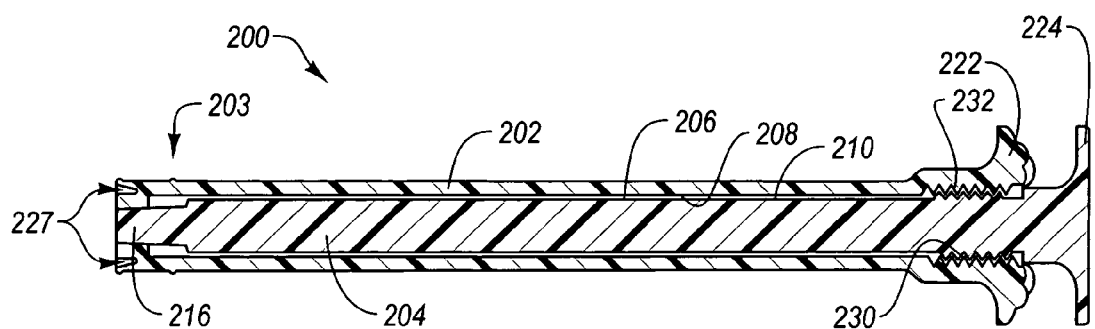
FIG. 2B is a cross-sectional view of the vented plunger assembly of FIG. 2A in a closed position.
Figure 2C:
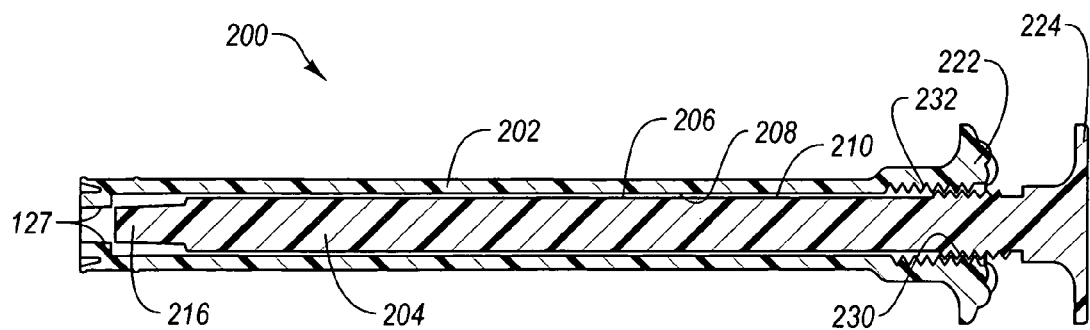
FIG. 2C is a cross-sectional view of the vented plunger assembly of FIG. 2A in an open position.

FIGS. 2A-2C illustrate an alternative venting syringe plunger assembly 200 including an outer sleeve 202, an inner stem 204, and a venting passageway 206. Venting passageway 206 is bounded and defined by interior surface 208 of outer sleeve 202 and exterior surface 210 of inner stem 204. Outer sleeve 202 is illustrated as including a V-cup seal 227 for sealing outer sleeve 202 against an inner surface of a syringe barrel. A groove and elastomeric seal (not shown) may alternatively or additionally be included.

Exterior surface 210 includes threads 230 formed near the proximal end 201 of stem 204 (although they could be formed elsewhere on stem 204). Corresponding engagement grooves 232 are formed in interior surface 208, also near the proximal end 201 of sleeve 202. Threads 230 are configured to engage grooves 232, such that rotation of inner stem 204 within outer sleeve 202 causes the stem to move longitudinally within outer sleeve 202. Longitudinal movement of inner stem 204 within outer sleeve 202 selectively opens or closes venting passageway 206. Threads 230 and grooves 232 are another example of means for selectively moving inner stem 204 within outer sleeve 202 so as to selectively open or close venting passageway 206.

In the illustrated embodiment, inner stem 204 includes a luer cone 216 formed at distal end 203 of inner stem 204. When venting passageway 206 is in a closed configuration, luer cone 216 forms a seal with a portion of interior surface 208 near distal end 203. In the illustrated embodiment, this seal is formed when the distal end 203 of inner stem 204 mates with distal end 203 of outer sleeve 202. As opposed to the embodiment of FIGS. 1A-1D where the seal is opened when the distal portion 116 of inner stem 104 is extended beyond outer sleeve 102, the seal is opened in this embodiment by withdrawing the distal portion 216 into the interior of outer sleeve 202. Head 224 may include markings to indicate which direction of rotation is associated with an open position and which direction of rotation is associated with a closed position of venting passageway 206 (e.g., counter-clockwise to open, clockwise to close). FIG. 2B is a cross-sectional view with venting passageway 206 closed, and FIG. 2C is a cross-sectional view with venting passageway 206 opened.

Figure 3A:
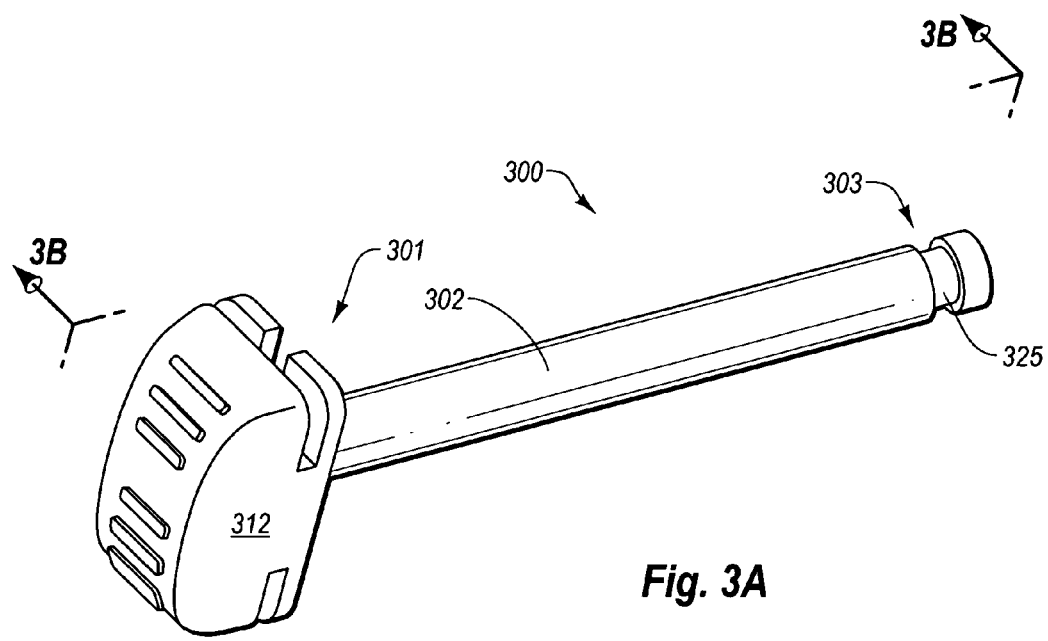
FIG. 3A is a perspective view of another exemplary vented plunger assembly.
Figure 3B:
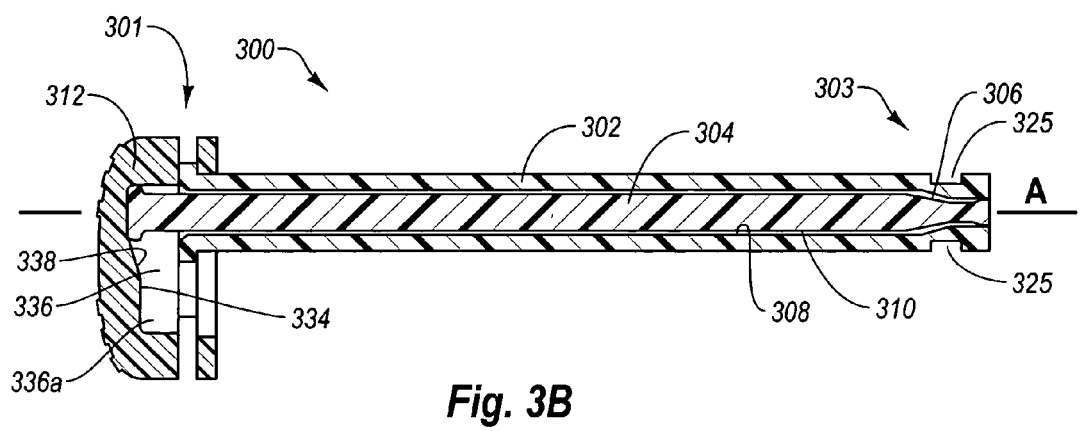
FIG. 3B is a cross-sectional view of the vented plunger assembly of FIG. 3A in a closed position.
Figure 3C:
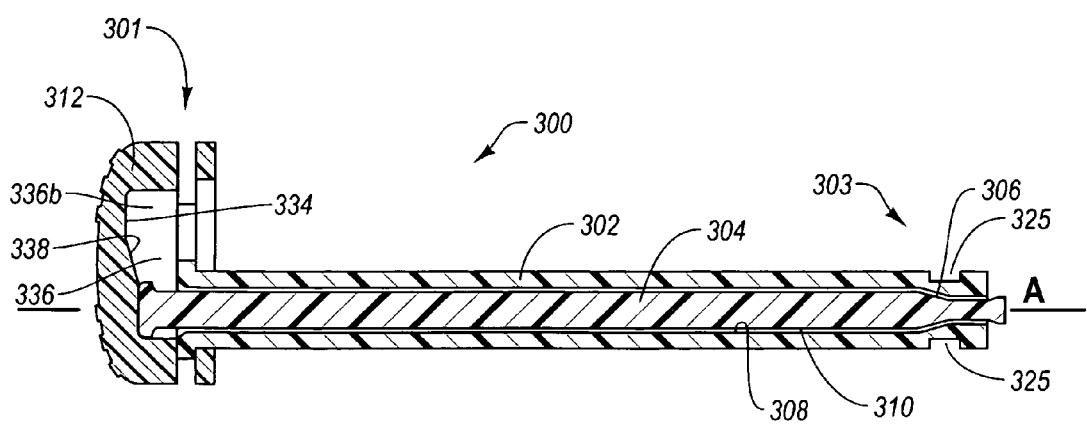
FIG. 3C is a cross-sectional view of the vented plunger assembly of FIG. 3A in an open position.

FIGS. 3A-3C illustrate an alternative venting syringe plunger assembly 300 including an outer sleeve 302, an inner stem 304, and a venting passageway 306. Venting passageway 306 is bounded and defined by interior surface 308 of outer sleeve 302 and exterior surface 310 of inner stem 304. Outer sleeve 302 is illustrated as including a groove 325 for receiving an elastomeric seal (e.g., an O-ring) for sealing outer sleeve 302 against an inner surface of a syringe barrel. A V-cup seal may alternatively or additionally be included.

Assembly 300 also includes a cam member 312 near the proximal end 301 of inner assembly 300. Operation of cam member 312 causes inner stem 304 to move longitudinally within outer sleeve 302 so as to selectively open and close venting passageway 306. Referring to FIGS. 3B-3C, cam member 312 includes an interior surface 334 bounding a cavity 336 within cam member 312. Inner stem 304 extends partially into cavity 336 such that the proximal end 301 of inner stem 304 contacts and is biased against interior surface 334. Interior surface 334 includes a ramped portion 338 dividing cavity 336 into a first cavity portion 336a of a first height and a second cavity portion 336b of a second height that is greater than the first height. Cam member 312 is slidable in an axis perpendicular to the longitudinal axis A of the outer sleeve 302 and inner stem 304.

Sliding cam member 312 causes the proximal end of inner stem 304 to slide along interior surface 334 such that the inner stem may be selectively moved from first cavity portion 336a over ramped portion 338 and into second cavity portion 336b. When inner stem 304 is within second cavity portion 336b, the distal end of inner stem 304 forms a seal with the distal end of outer sleeve 302, closing venting passageway 306 (FIG. 3B). Sliding cam member 312 so that the proximal end of inner stem 304 moves up ramped portion 338 and into first cavity portion 336a causes longitudinal movement of inner stem 304 within outer sleeve 302. When inner stem 304 is within first cavity portion 336a, the distal end of inner stem 304 extends beyond the distal end 303 of outer sleeve 304, opening venting passageway 306 (FIG. 3C). Cam member 312 can again be slid to the position illustrated in FIG. 3B to close venting passageway 306. Cam member 312 is another example of means for selectively moving inner stem 304 within outer sleeve 302 so as to selectively open or close venting passageway 306.

It will be readily appreciated that some embodiments (e.g., system 100 and system 300) allow operation of the means for selectively moving the inner stem within the outer sleeve (e.g., the cam member) with a single hand. Other embodiments (e.g., system 200) may be operated most conveniently through the use of two hands.

III. Exemplary Method of Use

Figure 4:
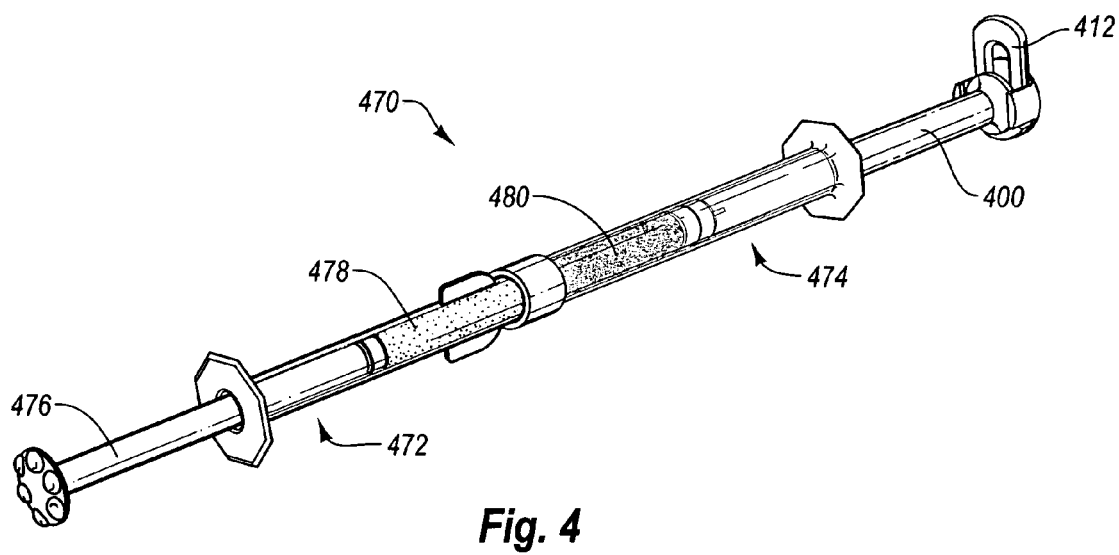
FIG. 4 is a perspective view of a syringe-to-syringe mixing system where one of the syringes includes a vented plunger.

FIG. 4 illustrates a syringe-to-syringe mixing system 470 including a first syringe 472 and a second syringe 474. First syringe 472 is illustrated as including a standard non-venting plunger 476, while second syringe 474 includes a venting plunger 400. A first component 478 may be loaded within the barrel of first syringe 472, and a second component 480 may be loaded within second syringe 474. Although illustrated in a configuration where only the second syringe 474 includes a vented plunger 400, it is to be understood that both syringes could alternatively include vented plungers.

The first syringe 472 and second syringe 474 are coupled together so that the barrel of the first syringe 472 is in fluid communication with the barrel of the second syringe 474 (and vice versa). The first and second plungers 476 and 400 respectively are then alternatingly advanced so as to pass the first and second components back and forth between the first and second syringes and mix the first and second components together. The first and second components may both be liquids, or one may be a liquid while the other is a powder. Additional exemplary syringe-to-syringe mixing systems are disclosed in U.S. Pat. Nos. 6,234,196; 6,305,413; and 6,610,034 and U.S. Patent Application Publication No. 2005/0119609, each of which is herein incorporated by reference with respect to disclosure of syringe-to-syringe mixing systems.

Figure 5:
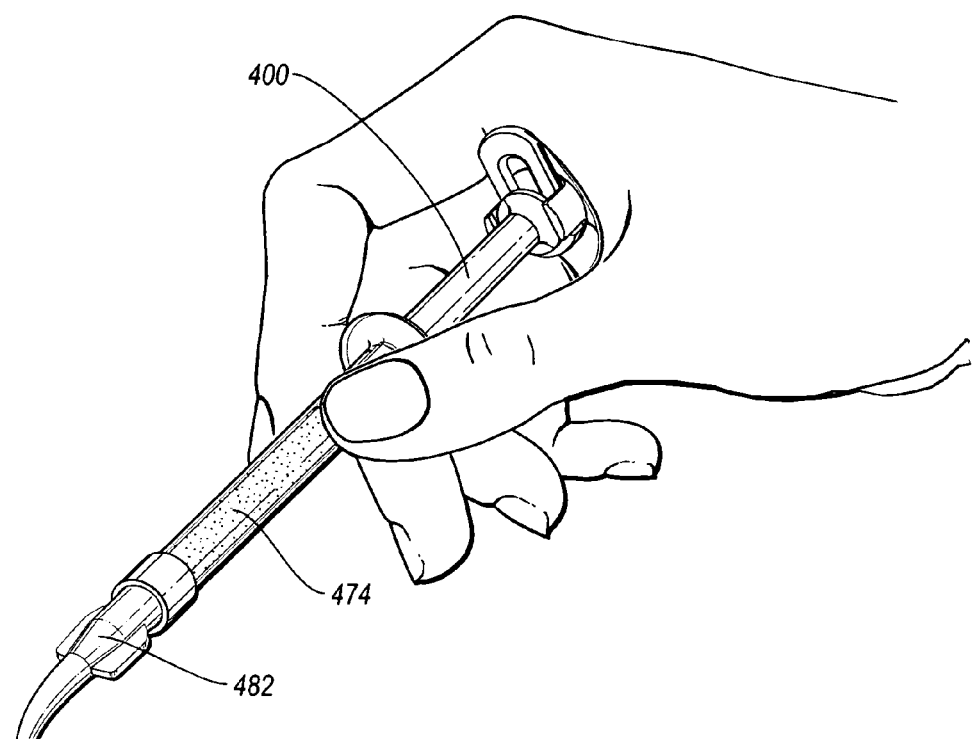
FIG. 5 is a perspective view of a syringe including a vented plunger being used to vent and dispense a composition.

Before or after the components 478 and 480 have been mixed together as desired, the venting passageway of the at least one venting plunger assembly 400 may be opened (e.g., by sliding cam member 412) so as to vent any air or gas contained within the syringe barrels. For example, if one of the components is a powder, air or gas initially present within the powder may actually be beneficial during mixing of the powder with a liquid as it may increase turbulence for more efficient mixing. However, once mixed, the continued presence of the air or gas may be detrimental. Such air or gas may be vented after mixing. The syringes may then be separated from each other, and the mixed composition may be dispensed from one of the syringes (e.g., syringe 474). If desired, a dispensing tip 482 may be coupled to the syringe, as illustrated in FIG. 5. Any trapped air or gas may be vented if necessary (e.g., additional air may have been introduced into the syringe barrel when coupling dispensing tip 482 to syringe 474 and/or additional gas may have been generated by the reaction of the two components).

It will be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. In a syringe-to-syringe mixing system that includes a first syringe loaded with a first component and a second syringe loaded with a second component, and wherein the two syringes are coupleable so that the barrel of the first is in fluid communication with the barrel of the second so as to permit mixing of the first and second components as the contents of one syringe barrel is injected into the other, at least one of the syringes comprising an improved vented plunger assembly situated within one of the syringe barrels of the syringe-to-syringe mixing system, the plunger assembly comprising:

a hollow outer sleeve which fits within the barrel of one of the syringes, the sleeve having an interior surface and means for sealing the hollow outer sleeve against an inner surface of the syringe plunger;

an inner stem disposed within the hollow outer sleeve so that the hollow outer sleeve and inner stem are operable to be alternately pushed together into the syringe barrel and withdrawn together from the barrel when used as a plunger assembly for performing a back and forth mixing action between syringe barrels of the first and second syringes, the inner stem having an exterior surface, the inner stem being movably disposed within the outer sleeve between open and closed positions;

a venting passageway being defined between the exterior surface of the inner stem and the interior surface of the hollow outer sleeve; and means for selectively moving the inner stem within the outer sleeve to either the open or closed positions and then temporarily locking the inner stem in the selected position, so that the venting passageway will remain in the selected open or closed position irrespective of whether the plunger assembly is thereafter pushed into our pulled out of the syringe barrel in which the plunger assembly is used.

2. A vented plunger assembly as recited in claim 1, the inner stem being slidable within the hollow outer sleeve.

3. A vented plunger assembly as recited in claim 1, the means for selectively moving the inner stem within the hollow outer sleeve so as to selectively open or close the venting passageway being capable of single hand operation.

4. A vented plunger assembly as recited in claim 1, the venting passageway being in an open configuration when a distal end of the inner stem is withdrawn into the hollow outer sleeve.

5. A vented plunger assembly as recited in claim 1, the venting passageway being in an closed configuration when a distal end of the inner stem is substantially flush with a distal end of the hollow outer sleeve or withdrawn into the hollow outer sleeve.

6. A vented plunger assembly as recited in claim 1, wherein the sealing means comprises a groove formed near a distal end of the hollow outer sleeve and an elastomeric seal seated within the groove.

7. A vented plunger assembly as recited in claim 1, wherein the sealing means comprises a V-cup seal formed at a distal end of the hollow outer sleeve.

8. A vented plunger assembly as recited in claim 1, the means for selectively moving the inner stem within the hollow outer sleeve comprising a cam member disposed near a proximal end of the inner stem and the hollow outer sleeve, the cam member being operable to move the inner stem within the hollow outer sleeve so as to selectively open and close the venting passageway.

9. A vented plunger assembly as recited in claim 8, the cam member being disposed between a head of the inner stem and a flange of the hollow outer sleeve.

10. A vented plunger assembly as recited in claim 9, the cam member further comprising a ramped lever slidable between the head of the inner stem and the flange of the hollow outer sleeve so as to move the inner stem within the hollow outer sleeve.

11. A vented plunger assembly as recited in claim 8, the cam member being retained by the inner stem such that the inner stem passes through the cam member, the cam member being slidable in a plane that is substantially perpendicular to a longitudinal axis of the inner stem.

12. A vented plunger assembly as recited in claim 8, the cam member encapsulating at least a portion of the hollow outer sleeve and the inner stem.

13. A vented plunger assembly as recited in claim 1, the means for selectively moving the inner stem within the hollow outer sleeve comprising threads formed on the exterior surface of the inner stem and corresponding engagement grooves formed in the interior surface of the hollow outer sleeve such that rotation of the inner stem within the hollow outer sleeve longitudinally moves the inner stem within the hollow outer sleeve so as to selectively open or close the venting passageway.

14. A vented plunger assembly as recited in claim 1, the inner stem including a luer cone at a distal end that is tapered so as to have a cross-sectional diameter that decreases towards the distal end of the inner stem for selectively forming a seal with the interior surface of the hollow outer sleeve so as to selectively close the venting passageway.

15. A vented plunger assembly as recited in claim 14, the vented plunger assembly being in an open configuration when the luer cone at a distal end of the inner stem is withdrawn into the hollow outer sleeve.

16. A vented plunger assembly as recited in claim 1, the inner stem including a tapered portion at the distal end of the inner stem, the tapered portion being tapered so as to have a cross-sectional diameter that increases towards the distal end of the inner stem.

17. A vented plunger assembly as recited in claim 16, the vented plunger assembly being in an open configuration when the tapered portion at the distal end of the inner stem is extended beyond a distal end of the outer sleeve.

18. In a syringe-to-syringe mixing system that includes a first syringe loaded with a first component and a second syringe loaded with a second component, and wherein the two syringes are coupleable so that the barrel of the first is in fluid communication with the barrel of the second so as to permit mixing of the first and second components as the contents of one syringe barrel is injected into the other, at least one of the syringes comprising an improved vented plunger assembly situated within one of the syringe barrels of the syringe-to-syringe mixing system, the plunger assembly comprising:

a hollow outer sleeve which fits within the barrel of one of the syringes, the sleeve having an interior surface and a flange near a proximal end of the outer sleeve;

an inner stem disposed within the hollow outer sleeve so that the hollow outer sleeve and inner stem are operable to be alternately pushed together into the syringe barrel and withdrawn together from the barrel when performing a back and forth mixing action between syringe barrels of the first and second syringes, the inner stem having an exterior surface and a head near a proximal end of the inner stem, the inner stem being movably disposed within the outer sleeve between open and closed positions;

a venting passageway being defined between the exterior surface of the inner stem and the interior surface of the hollow outer sleeve; and a cam member disposed between the flange of the outer sleeve and the head of the inner stem, the cam member including a ramped lever operable to move the inner stem within the hollow outer sleeve so as to selectively move the inner stem within the outer sleeve to either the open or closed position and operable to then temporarily lock the inner stem in the selected position, so that the venting passageway will remain in the selected open or closed position irrespective of whether the plunger assembly is thereafter pushed into our pulled out of the syringe barrel in which the plunger assembly is used.

19. In a syringe-to-syringe mixing system that includes a first syringe loaded with a first component and a second syringe loaded with a second component, and wherein the two syringes are coupleable so that the barrel of the first is in fluid communication with the barrel of the second so as to permit mixing of the first and second components as the contents of one syringe barrel is injected into the other, at least one of the syringes comprising an improved vented plunger assembly situated within one of the syringe barrels of the syringe-to-syringe mixing system, the plunger assembly comprising:

a hollow outer sleeve which fits within the barrel of one of the syringes, the sleeve having an interior surface;

an inner stem disposed within the hollow outer sleeve so that the hollow outer sleeve and inner stem are operable to be alternately pushed together into the syringe barrel and withdrawn together from the barrel when performing a back and forth mixing action between syringe barrels of the first and second syringes, the inner stem having an exterior surface, the inner stem being movably disposed within the outer sleeve between open and closed positions;

a venting passageway being defined between the exterior surface of the inner stem and the interior surface of the hollow outer sleeve; and threads formed on the exterior surface and near a proximal end of the inner stem and corresponding engagement grooves formed in the interior surface and near a proximal end of the hollow outer sleeve such that rotation of the inner stem within the outer sleeve longitudinally moves the inner stem within the outer sleeve so as to selectively move the inner stem within the outer sleeve to either the open or closed position and operable to temporarily lock the inner stem in the selected position, so that the venting passageway will remain in the selected open or closed position irrespective of whether the plunger assembly is thereafter pushed into our pulled out of the syringe barrel in which the plunger assembly is used.

\* \* \* \* \*

UNITED STATES PATENT AND TRADEMARK OFFICE
CERTIFICATE OF CORRECTION

PATENT NO. : 7,503,905 B2
APPLICATION NO. : 11/242255
DATED : March 17, 2009
INVENTOR(S) : Jessop et al.

It is certified that error appears in the above-identified patent and that said Letters Patent is hereby corrected as shown below:

Column 2
Line 64, before "mixing", remove [o m]

Column 3
Line 24, change "full" to --fully--

Signed and Sealed this

First Day of December, 2009

David J. Kappos
*Director of the United States Patent and Trademark Office*